United States Patent [19]
Sultan et al.

[11] Patent Number: 5,343,760
[45] Date of Patent: Sep. 6, 1994

[54] GAS CONCENTRATION AND FLOW RATE SENSOR

[75] Inventors: Michel F. Sultan, Troy; Joseph L. Kenty, Birmingham; Michael J. O'Rourke, Warren, all of Mich.

[73] Assignee: General Motors Corporation, Detroit, Mich.

[21] Appl. No.: 910,913

[22] Filed: Jul. 9, 1992

[51] Int. Cl.[5] .................... G01F 1/74; G01N 29/02
[52] U.S. Cl. .................... 73/861.04; 73/24.01
[58] Field of Search ........... 73/861.18, 861.21, 861.04, 73/24.01, 24.05

[56] References Cited

U.S. PATENT DOCUMENTS

| | | | |
|---|---|---|---|
| 2,779,917 | 1/1957 | Boisblanc | 324/40 |
| 3,468,157 | 9/1969 | Burk et al. | 73/24.01 |
| 3,580,075 | 5/1971 | Steinberg | 73/339 |
| 3,580,092 | 5/1971 | Scarpa | 73/194 |
| 4,380,167 | 4/1983 | Longini | 73/24 |
| 4,462,261 | 7/1984 | Keyes et al. | 73/861.02 |
| 4,663,977 | 5/1987 | Vander Heyden | 73/861.03 |
| 4,742,717 | 5/1988 | Ichino | 73/861.18 |
| 4,896,540 | 1/1990 | Shakkottai et al. | 73/861.18 |
| 5,207,107 | 5/1993 | Wolf et al. | 73/861.18 |

FOREIGN PATENT DOCUMENTS 139107 11/1966 U.S.S.R. .

OTHER PUBLICATIONS

U.S. Patent Application Ser. No. 07/829,670 filed Feb. 3, 1992, entitled "Apparatus for Determining Gas Concentrations" by Michel F. Sultan, Joseph L. Kenty, David S. Eddy, and John W. Hile.

Primary Examiner—Richard E. Chilcot, Jr.
Assistant Examiner—Harshad Patel
Attorney, Agent, or Firm—Howard N. Conkey

[57] ABSTRACT

A gas vapor sensor indicates the relative concentrations and flow rate of a gas mixture. Acoustic noise is generated within a closed chamber by the gas mixture flowing therethrough or by ambient noise sources. The chamber has a fundamental resonant frequency which varies with the vapor concentration. Acoustic frequency components of the noise corresponding to the resonant frequency of the chamber are sharply reinforced and dominate the acoustic spectrum within the chamber. The spectrum is detected and frequency filtered by a pair of dissimilar parallel filters to produce two attenuated outputs. The difference between the attenuated outputs indicates the resonant frequency and is a measure of the vapor concentration. The strength of the acoustic spectrum together with the measured vapor concentration indicates the flow rate of the mixture.

10 Claims, 4 Drawing Sheets

GAS CONCENTRATION AND FLOW RATE SENSOR

BACKGROUND OF THE INVENTION

This invention relates to the measurement of a gas mixture for the determination of concentrations of individual predetermined constituent gases and flow rate of the mixture. The invention is especially directed to a method and apparatus for such measurement in which acoustic attributes of the gas mixture and flow thereof are utilized to derive the desired quantities.

One particularly useful application for measurement of gas concentrations and flow rate is in an automobile's evaporative emissions management system. In such a system, fuel vapor is captured in a canister to prevent its release into the atmosphere. To purge the fuel vapor, intake vacuum is typically applied to the canister which draws the fuel vapor out of the canister and into the engine where it is utilized as part of the fuel charge. Canister purge may result in a rich fuel charge if vapor concentrations are heavy resulting in increased exhaust emissions and reduced quality of driveability. A fuel vapor concentration and flow rate sensor may, therefore, be useful for additional control and monitoring of the introduction of recovered fuel vapor into an engine.

It is well known that the velocity (V) of sound propagating through a gas mixture can be expressed as a relationship between the mixture's specific heats at constant pressure ($C_{pm}$) and volume ($C_{vm}$), average molecular mass ($M_m$), absolute temperature (T) and the universal gas constant (R) as follows:

$$V = \frac{[R*T*C_{pm}]^{\frac{1}{2}}}{[M_m*C_{vm}]^{\frac{1}{2}}} \tag{1}$$

The individual properties of each constituent gas in the mixture are weighted according to the constituent gas volume fraction (x) and summed to arrive at the specific heats and average molecular mass of the gas mixture as follows:

$$C_{pm} = x_1C_{p1} + x_2C_{p2} + \ldots + x_iC_{pi} \tag{2}$$
$$C_{vm} = x_1C_{v1} + x_2C_{v2} + \ldots + x_iC_{vi} \tag{3}$$
$$M_m = x_1M_1 + x_2M_2 + \ldots + x_iM_i \tag{4}$$

where $$x_1 + x_2 + \ldots + x_i = 1 \tag{5}$$

For a binary mixture of gases, equations (1) through (5) reduce to the following equation in terms of the volume fraction of one of the two gases:

$$V = \frac{[R*T(x_1C_{p1} + (1 - x_1)C_{p2})]^{\frac{1}{2}}}{[(x_1M_1 + (1 - x_1)M_2)*(x_1C_{v1} + (1 - x_1)C_{v2})]^{\frac{1}{2}}} \tag{6}$$

where subscripts 1 and 2 designate the first and second gases, respectively, in the gas mixture.

If a gas mixture is bounded by a vessel, resonant modes exists which are dependent upon the vessel geometry and the sound velocity therein. For a pipe of length (L) closed at both ends bounding a gas mixture, the lowest order resonant mode, or fundamental resonant frequency ($F_{res}$) is expressed as follows:

$$F_{res} = \frac{V}{2*L} \tag{7}$$

Equations (6) and (7) reduce to:

$$F_{res} = \frac{[R*T(x_1C_{p1} + (1 - x_1)C_{p2})]^{\frac{1}{2}}}{2*L[(x_1M_1 + (1 - x_1)M_2)*(x_1C_{v1} + (1 - x_1)C_{v2})]^{\frac{1}{2}}} \tag{8}$$

A measurement of the fundamental resonant frequency where the two gases are known leaves the first gas volume fraction ($x_1$) as the only unknown in equation (8). Therefore, a determination of the fundamental resonant frequency indicates the gas volume fraction. Higher order resonant modes also exist which are related to dimensions of the bounding vessel. Lower frequency resonant modes related to the volume of the vessel are also present. In similar fashion, determination of these resonant modes would indicate the gas volume fraction.

U.S. Pat. No. 4,380,167 shows an open ended tube device which relies upon velocity of sound through a gas to determine gas concentrations. This device utilizes narrowband ultrasonic signals generated by a transducer which excite the gases at some ultrasonic frequency and requires a tube of specific unit lengths said to be related to the natural resonant frequency wavelength of the particular gas whose fraction is being measured. This device is said to detect resonance by amplitude threshold detection. This device is limited in the gas concentration range it can detect because of its dependence upon the limited narrowband excitation signal developed by an ultrasonic transmitter. It follows then that the device is inadequate to detect wide range variations in gas concentrations such as from 0 to 100 percent.

Prior art devices to measure flow rate of gases based upon sound velocity through the gas have at least a pair of transducers located some distance apart relative to the central axis of a gas carrier tube or pipe, one being downstream from the other. The transducers alternately transmit and receive ultrasonic signals and a flow velocity is derived from the difference in sound propagation times upstream to downstream and downstream to upstream. More complicated devices utilize an upstream and a downstream multiple transducer array wherein each transducer, in turn and to the exclusion of the remaining transducers, acts as a transmitter to all remaining transducers which act as receivers. Such an arrangement is said to improve accuracy of flow measurements since derivations are based upon multiple propagation paths through various flow patterns, thus providing more complete flow profile data. Pertinent references include: U.S. Pat. No. 4,742,717 to Ichino; U.S. Pat. No. 4,663,977 to Vander Heyden; and U.S. Pat. No. 4,462,261 to Keyes et al. These references rely upon transducers to excite the subject gas and appear to be directed toward flow measurement of a single gas or proportionally stabilized mixture of gases.

U.S. Pat. No. 3,580,092 to Scarpa shows a flow monitoring device which secures to an external surface of a pipe to detect ultrasonic noise caused by shear action of a fluid flowing therein. The device relies upon a flow rate sufficient to generate an acoustic signal of adequate intensity to be accurately detected and does not benefit from acoustic reinforcement such as system resonance would provide.

SUMMARY OF THE INVENTION

In general, this invention provides an improved method and apparatus for detecting, separately or in combination, relative gas concentrations and flow rates of a binary gas mixture by passing the gas mixture through a chamber and detecting the fundamental resonant frequency and strength of sound coupled therein, the fundamental resonant frequency being primarily dependent upon the relative concentrations of the individual gas constituents of the mixture and the intensity being dependent upon the relative concentrations and flow rate of the gas mixture. The fundamental resonant frequency provides a measure of the relative concentrations of the two gases. The strength of sound coupled within the chamber at a particular concentration is utilized to approximate the flow rate of the gas mixture therethrough.

In one aspect of the invention, necessary acoustic excitation of the mixture is achieved without employing any transducers to acoustically stimulate the mixture. Sound is coupled within the chamber from inherent noise generated by the flow of the mixture through the chamber or from ambient noise sources. In a specific form of the invention, the chamber takes the form of a cylinder closed at both ends. The gas mixture to be measured is passed through the chamber via inlet and outlet ports adjacent to respective ends of the cylinder, the flow of the gas mixture producing necessary acoustic excitation within the chamber. Acoustic noise is detected and amplified at least within a certain spectrum of frequencies to produce an electrical signal representative of the actual acoustic signal in the chamber, hereafter referred to as the spectrum signal. The spectrum signal is then processed such as by parallel filtering means and differential amplification means to derive therefrom a signal representative of the fundamental resonant frequency which indicates the gas concentrations of the mixture. The strength of the spectrum signal together with the sensed gas concentrations provides a measure of the flow rate of the mixture.

In another aspect of this invention, the purge gas output of a vehicle fuel vapor storage canister of a vehicle is passed through the chamber so that the determined resonant acoustic frequency of the chamber is a measure of the air and fuel vapor drawn into the vehicle engine and the strength of the signal is a measure of the rate at which that air and fuel vapor is drawn into the vehicle engine during fuel vapor purge of the canister.

Further details and advantages of the invention will be apparent from the accompanying drawings and following description of the preferred embodiment.

DETAILED DESCRIPTION OF THE PREFERRED EMBODIMENT

Figure 1:
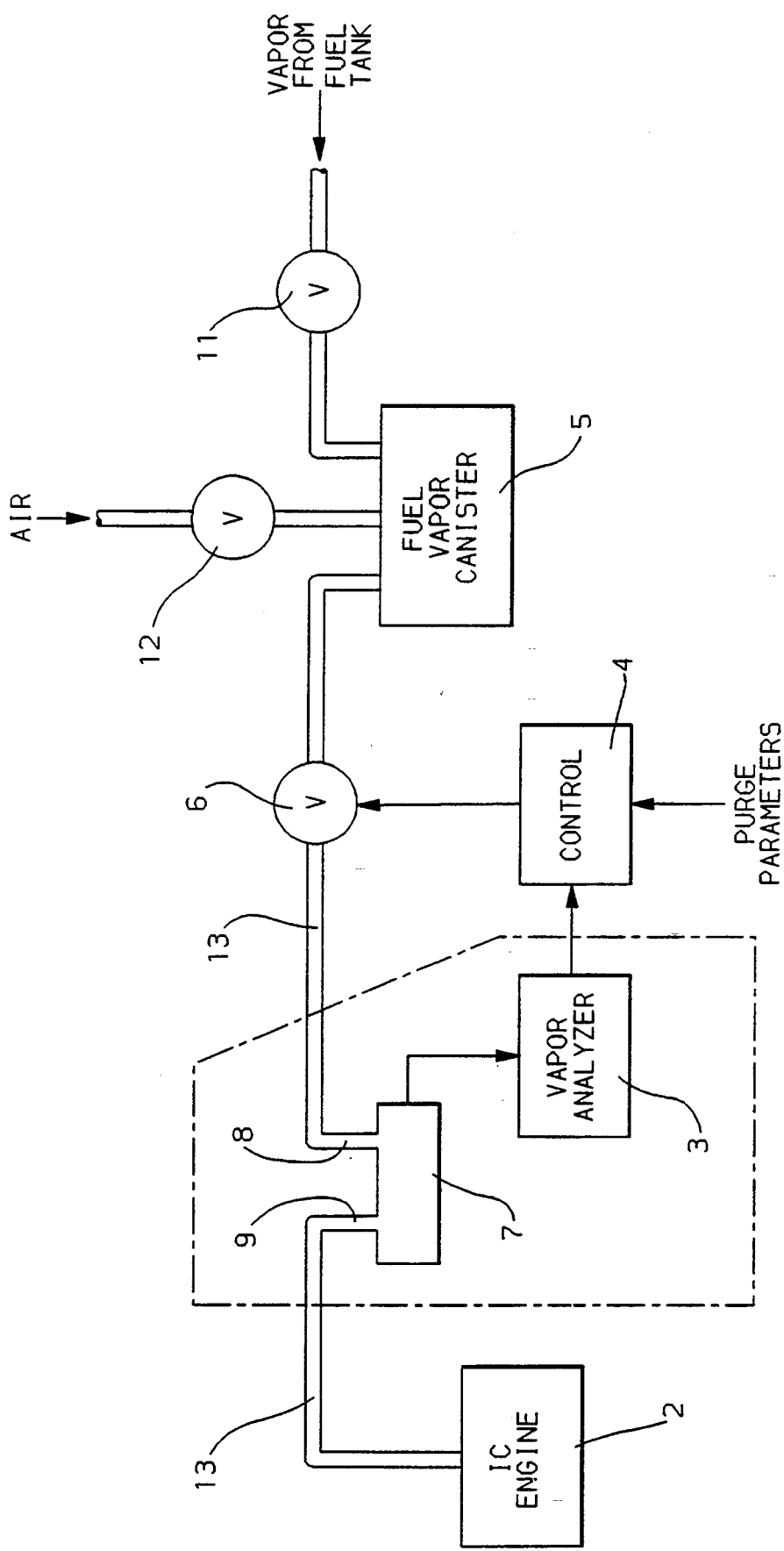
FIG. 1 is a block diagram of a fuel vapor concentration and flow rate sensing apparatus according to the invention.

Referring to FIG. 1, the gas concentration and flow rate sensor of this invention is shown as part of a fuel vapor canister purge system for internal combustion engine vehicles. Fuel vapor (primarily butane) from fuel tank (not shown) passes through pressure relief valve 11 to be captured in fuel vapor canister 5. Engine 2 supplies vacuum to fuel vapor canister through valve 6 such that air is drawn through fuel vapor canister via check valve 12 and the resultant vapor mixture of air and fuel is delivered to engine 2 via vapor line 13 for combustion. Valve 6 is opened and closed by control 4 which may be part of an overall fuel delivery control system typically controlling purge of fuel vapor canister 5 in response to such purge parameters as engine temperature, road speed, throttle angle and exhaust gas composition. The foregoing is generally illustrative of fuel vapor recovery and purge for an internal combustion engine vehicle.

Figure 2:
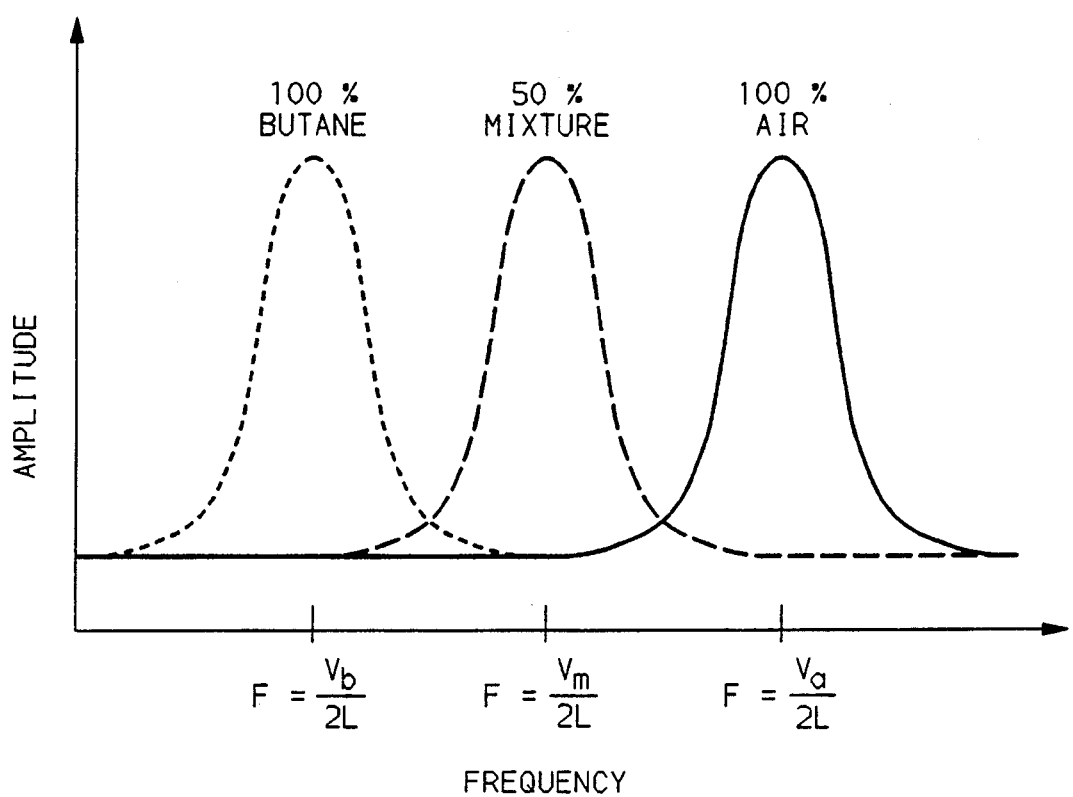
FIG. 2 is a graphical representation of resonance and attenuation of noise within a chamber according to the invention.

The invention is demonstratively exemplified with respect to measuring a butane/air gas mixture; however, it is noted that other constituent gases may readily be detected according to sensor application within the ambit of the invention. The present invention is therefore represented generally and in application to fuel vapor purge by the broken line boxed portion of FIG. 1. Chamber 7, having inlet 8 adjacent one end of the chamber and outlet 9 adjacent the other end of the chamber, is placed in vapor line 13 such that the vapor delivered to engine 2 passes through chamber 7. The chamber has a fixed length (L) and a fundamental resonant frequency dependent upon the vapor concentration therein. When vapor flows through the chamber, noise is generated therein having broad spectral components. That is to say the noise attributable to flow has frequency components spanning at least the range of resonant frequencies of interest corresponding to the range of gas concentrations to be measured. Those frequency components equal to or approaching the fundamental resonant frequency of the chamber will be sharply reinforced in a standing wave pattern while frequency components more removed from the fundamental resonant frequency of the chamber will be attenuated or damped. Thus the frequency components very near the fundamental resonant frequency will have a sharply higher amplitude relative to those frequency components further removed. The correspondence between fundamental resonant frequency and vapor concentration can be exploited for determination of vapor concentration. FIG. 2 illustrates this concept graphically for vapor concentrations of 100% butane, 100% air, and 50% of each butane and air.

The velocities of sound through 100% butane and 100% air at room temperature are 216 m/s and 348 m/s respectively and correspond to the minimum and maximum velocities of sound through a mixture of butane and air. It is desirable to establish a convenient chamber length (L) and, in the instant application to fuel vapor sensing, a length of 14.8 cm is chosen. This length is relatively easily packaged in a vehicle and yields fundamental resonant frequencies ranging approximately from 730 Hz to 1175 Hz corresponding to 100% butane and 100% air respectively according to preceding formula (7). Other chamber lengths may be employed with the result that shorter lengths will shift fundamental resonant frequencies higher and longer lengths will shift these frequencies lower.

The strength of the noise generated by flow of the vapor increases with increasing flow rate. The strength of the noise is also dependent upon the vapor concentrations present within the chamber with stronger acoustic signals present at higher concentrations of the heavier constituent gas, in the present example butane. The correspondence between the strength of noise and flow rate at a predetermined vapor concentration can be exploited for determination of flow rate. At low flow rates the strength of noise generated by flow may be on the same order of magnitude as noise from ambient sources. For this reason, if low flow rates are to be measured, constriction of the inlet, outlet or chamber, or incorporation of a whistling device is desirable so that the predominant noise detected is attributable to flow.

Vapor analyzer 3 detects an acoustic signal from within chamber 7 generated by the flow of vapor therein, processes the signal and provides output signals representative of chamber fundamental resonant frequency and strength of noise within the chamber usable for control purposes. As applied in FIG. 1, such output signals provide additional input to control 4 for improved control of vacuum application and consequent purge of fuel vapor canister 5.

Figure 3:
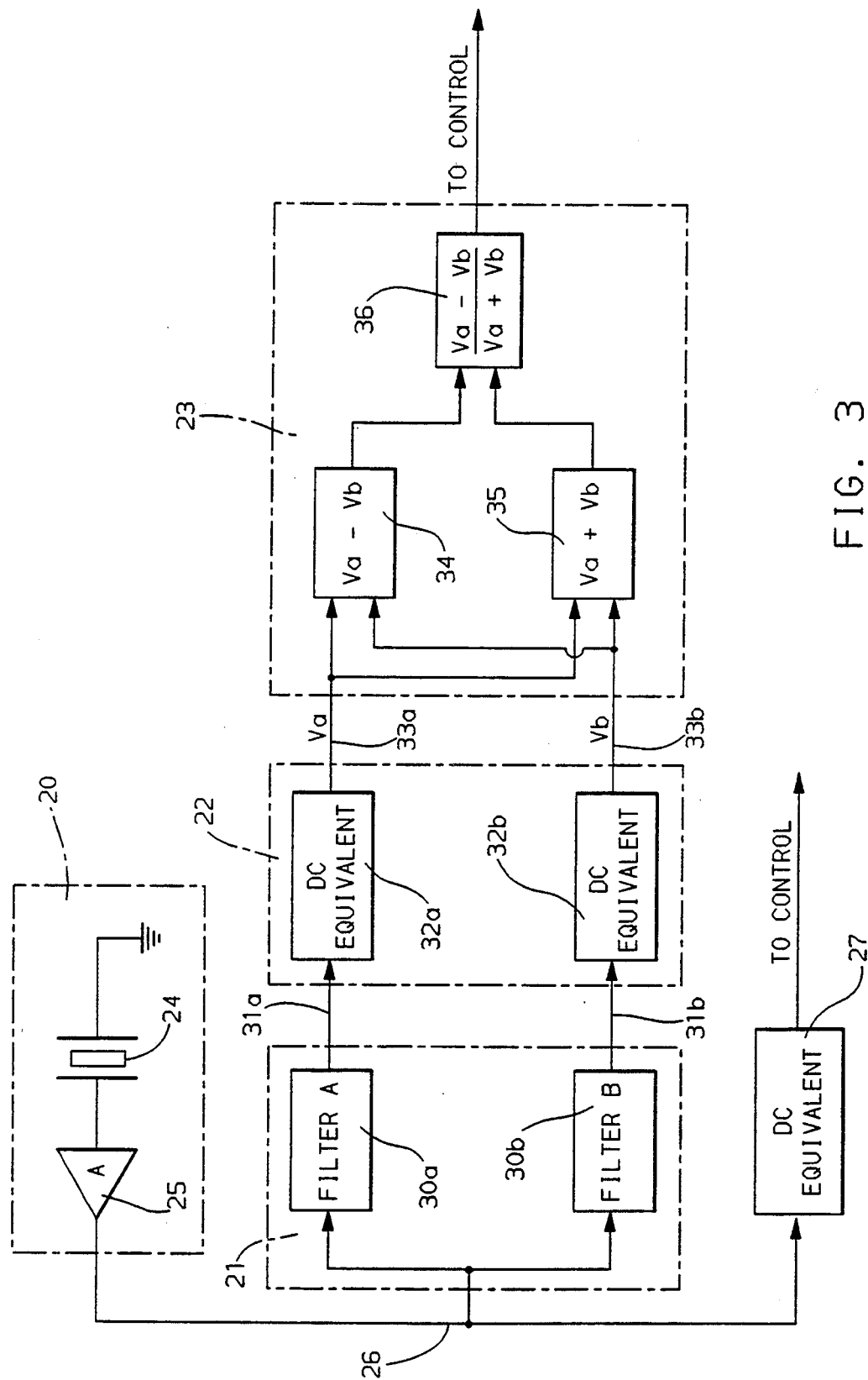
FIG. 3 shows a first embodiment of an apparatus for sensing gas concentrations and flow rates as shown in FIG. 1.

Referring to FIG. 3, spectrum signal generator 20 has transducer 24 acoustically coupled to the chamber and providing a low level AC voltage signal to amplifier 25, the output of which is the spectrum signal 26. The preferred choice for transducer 24 is a broadband transducer covering at least the range of frequencies to be detected. A piezoelectric crystal secured to the external surface of a thin diaphragm forming one closed end of the chamber is advantageous for this application, provided its own fundamental resonant frequency is outside the range of frequencies to be detected. Locations other than the ends of the chamber, which maximize coupling of the acoustic signal to the transducer, may also be utilized within the scope of the invention. While piezoelectric transducers may offer size, cost durability, availability and convenience advantages over other types of transducers, other transducers may be employed with satisfactory results.

The spectrum signal is coupled to parallel filtering circuit 21. Parallel filtering circuit 21 has two filters 30a and 30b with respective inputs coupled together and further coupled to the spectrum signal whereby each filter processes the identical input. Each one of the filters 30a and 30b has a response curve which is monotonic and different at least in slope from the other over the range of resonant frequencies to be sensed. Each one of the parallel filters 30a and 30b produces a respective attenuated spectrum output signal 31a and 31b whose signal strengths are attenuated according to the respective filter response curve. With filter response curves as described and with unvarying strength of the spectrum signal irregardless of fundamental resonant frequency, the difference between the signal strengths of the respective attenuated spectrum outputs at any particular fundamental resonant frequency will be unique from the difference between the signal strengths of respective attenuated spectrum outputs at any other fundamental resonant frequency within the range to be sensed. This difference can be exploited to indicate the fundamental resonant frequency of the chamber.

The sensitivity of the difference between the signal strengths of the respective attenuated spectrum outputs to a shift in fundamental resonant frequency is dependent upon the difference as between the respective slopes of the two filter's response curves. Filters whose response curves converge and/or diverge most rapidly offer the greatest sensitivity when measuring the difference between the signal strengths of respective attenuated spectrum outputs. For this reason, preferably one of the filters has a response curve whose slope is relatively steep and negative within the range of frequencies to be sensed and the other of the filters has a response curve whose slope is relatively steep and positive within the range of frequencies to be sensed.

Figure 4:
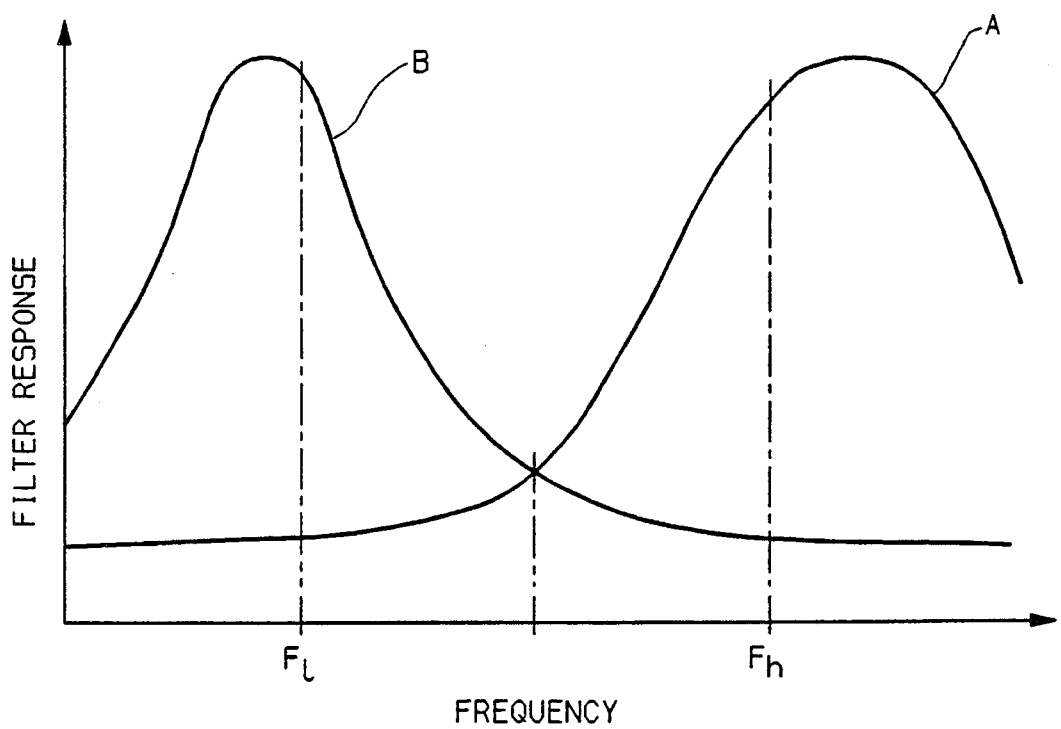
FIG. 4 is a graphical representation of filter response curves according to the invention.

As shown in FIG. 4, two typical filter response curves are superimposed such that response curve A corresponding to filter 30a has a monotonic portion with a positive slope between the lowest ($F_l$) and highest ($F_h$) fundamental resonant frequencies to be sensed. Response curve B corresponding to filter 30b has a monotonic portion with a negative slope also between $F_l$ and $F_h$. Each response curve represents the degree of attenuation of an identical spectrum signal and the relative signal strength of each respective filter's attenuated spectrum output versus resonant frequency. The difference between the signal strengths of attenuated spectrum outputs according to response curves B and A varies from a large positive value at $F_l$ to a large negative value at $F_h$ with a value of zero at the fundamental resonant frequency the two response curves intersect. $F_l$ and $F_h$ are, for a chamber length of 14.8 cm, approximately 730 Hz and 1175 Hz respectively. Filter 30a and filter 30b are therefore designed such that the appropriately sloped substantially linear portions of the response curves fall between 730 Hz and 1175 Hz.

Figure 5:
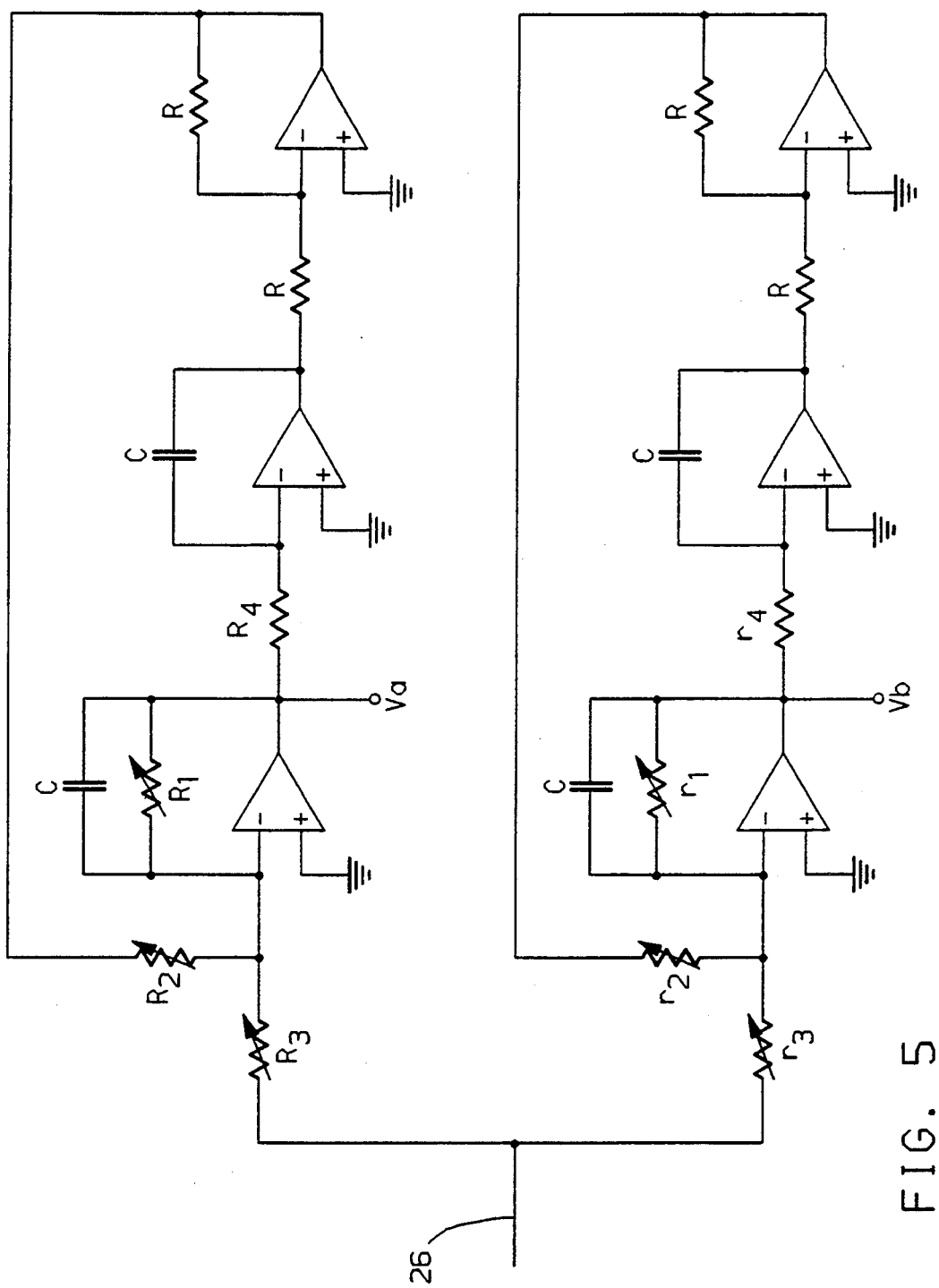
FIG. 5 shows a first embodiment of a parallel filter circuit according to the invention.

An active parallel filter circuit is shown in FIG. 5 which will result in response curves of the character illustrated in FIG. 4 and described above. The filters are independent bandpass filters, filter 30b having a central frequency ($F_{cl}$) of substantially the lowest fundamental resonant frequency $F_l$ to be sensed and filter 30a having a central frequency ($F_{ch}$) of substantially the highest fundamental resonant frequency $F_h$ to be sensed. Preferably, each filter response curve central frequency is shifted slightly outside the range of fundamental resonant frequencies to be sensed in order to place the steepest sloping and monotonic portion of each response curve within the range. Conventional operational amplifiers serve as the basis for the active filters shown in FIG. 5. Specific component values of each filter circuit are not given here since they can effectively be selected to obtain the desired respective central frequencies ($F_{cl}$, $F_{ch}$), slope or quality factor ($Q_l$, $Q_h$) and gain ($G_l$, $G_h$) according to the following relationships which are well known to those skilled in the art.

$$F_{cl} = \frac{1}{2*pi*C(R_2*R_4)^{\frac{1}{2}}} \quad (9)$$

$$F_{ch} = \frac{1}{2*pi*C(r_2*r_4)^{\frac{1}{2}}} \quad (10)$$

$$Q_l = \frac{R_1}{(R_2*R_4)^{\frac{1}{2}}} \quad (11)$$

$$Q_h = \frac{r_1}{(r_2*r_4)^{\frac{1}{2}}} \quad (12)$$

$$G_l = \frac{R_1}{R_3} \quad (13)$$

$$G_h = \frac{r_1}{r_3} \quad (14)$$

In the present embodiment, filter 30b central frequency $F_{cl}$ is set at 700 Hz, and filter 30a central frequency $F_{ch}$ is set at 1250 Hz, both central frequencies being slightly outside the range of resonant frequencies to be sensed in order to ensure the most linear portion of each response curves is between $F_l$ and $F_h$. Both filters have a quality factor of 4 and gain of 10. The quality factor determines slope of the response curve and the gain is chosen to provide an adequate output signal level. Filter designs other than those illustrated, such as low pass and high pass filters may also be utilized as may filter designs differing in detail but similar in function. Filter design specifics are readily achievable by those having ordinary skill in the area of filter design or similar circuitry.

Attenuated spectrum output signals 31a and 31b are multiple frequency AC voltage signals. Difference calculations of such AC voltage signals are best accomplished by first establishing the equivalent DC voltage values, $V_a$ 33a and $V_b$ 33b, of the AC voltage signals as indicated by the broken lined portion 22 of FIG. 3. The difference between the attenuated spectrum output signals is then established from the DC voltage values $(V_a - V_b)$. As noted earlier, assuming unvarying spectrum signal strength of the spectrum signal at all resonant frequencies to be sensed, the difference at a particular resonant frequency will be unique from the difference at any other resonant frequency. However, it is expected that the spectrum signal will vary in strength since it is known that the intensity of the noise generated by flow of the vapor increases with increasing flow rate. In order to establish an output signal insensitive to varying spectrum signal strength, normalization of the difference signal with respect to the spectrum signal is desirable. A normalized difference signal is therefore achieved by establishing the ratio of the difference of the DC voltage values $(V_a - V_b)$ to the sum of the DC voltage values $(V_a + V_b)$. These mathematical functions performed with $V_a$ and $V_b$ may be performed as indicated by the broken line portion 23 of FIG. 3.

One way of establishing the DC voltage values $V_a$ and $V_b$ as in 22 and performing all mathematical functions with $V_a$ and $V_b$ as in 23 is by conventional laboratory spectrum analyzer equipment programmed to calculate the DC values $V_a$ and $V_b$ of the two attenuated spectrum signal outputs, calculate the difference between $V_a$ and $V_b$, calculate the sum of $V_a$ and $V_b$, and divide the difference by the sum to establish the normalized difference indicating the resonant frequency and thus the vapor concentration. Another way of accomplishing these functions, and one better suited to the present application to on-vehicle sensing, is by commercially available analog electronics. For example, discrete circuits such as rectifiers and low pass filters can be utilized to in flow measurements establish DC voltage values as in 22. One commercially available integrated device which performs this function is the Analog Devices AD736 true RMS to DC converter chip which converts an AC signal to its DC equivalent. Conventional operational amplifiers are readily configured to accept the DC voltages ($V_a$ and $V_b$) and perform analog addition and subtraction with $V_a$ and $V_b$ to establish a difference voltage ($V_a - V_b$) and a sum voltage ($V_a + V_b$) therefrom. A commercially available chip, such as the Analog Devices AD532 ratio chip, can be used to perform division of the difference voltage from the sum voltage and produce the desired normalized difference voltage. The normalized difference voltage will vary from a large negative value at the lowest resonant frequency to be sensed to a large positive value at the highest resonant frequency to be sensed. The value of the normalized difference voltage indicates the resonant frequency of the chamber. In the present application to on-vehicle sensing, the normalized difference voltage comprises an input to control 4, whose value indicates the vapor concentration of the mixture.

The strength of the noise generated by the flow of the gas mixture increases with increasing flow and also increases with increasing concentrations of the heavier constituent gas, in the present example butane. Knowing the strength of the noise generated by flow is not, in itself, sufficient to accurately approximate flow rate therefrom. However, where the vapor concentration is known, the flow rate can be accurately approximated as a function of the strength of the noise at the known vapor concentration. A convenient manner of establishing the flow rate is through control 4 by way of a conventional two dimensional look-up table or matrix, the values of which can be established empirically. Improved accuracy of flow rate measurement and minimization of look-up table size may be achieved by using a combination of conventional look-up table and interpolation techniques. In either manner, the look-up table may be addressed or referenced in one dimension by the value of the normalized difference voltage representing the known vapor concentration and in the other dimension by a measure of the strength of the spectrum signal representing the strength of the noise as generated by the flow of the gas mixture.

The strength of the spectrum signal, a multiple frequency AC voltage signal, is most readily represented by its equivalent DC voltage value as indicated by block 27 in FIG. 3. Therefore, as similarly done with the attenuated output signals, conventional laboratory spectrum analyzer equipment programmed to calculate the DC value of the spectrum signal is one preferred way of establishing the strength of the spectrum signal. Another preferred way of establishing the spectrum voltage, and again one better suited to the present application to on-vehicle sensing, is by commercially available analog electronics. Rectification and low pass filtering can be utilized to establish a DC voltage or a commercially available integrated device such as the Analog Devices AD736 true RMS to DC converter chip may be used. In the present application to on-vehicle sensing, the spectrum voltage comprises an input to control 4, whose value, together with the normalized difference voltage value, indicates the flow rate of the mixture such as through a conventional look-up table alone or in combination with interpolation techniques.

The preferred embodiment for application to on-vehicle sensing has been described with reference to analog processing. Digital processing means can also be employed within the scope of the invention. For example, subsequent to establishing equivalent DC voltage values for the AC attenuated spectrum signals, the DC voltage may be digitally quantified such as by conventional A/D converters. All mathematical functions as in 23 can then be performed in the digital domain such as by conventional microprocessor circuitry. These mathematical functions may be readily handled by control 4, requiring only A/D conversion of the DC voltages for input to control 4. Likewise, the spectrum signal's equivalent DC voltage can be converted digitally and input to control 4.

As indicated by equation (8), the resonant frequency is also affected by the square root of absolute temperature. This translates into shifts in the resonant frequency for any given vapor concentration and, ultimately, changes in the normalized difference voltage. Compensation for the effects of temperature are desirable in order to ensure sensor accuracy. One possible way to establish a temperature insensitive sensor is by causing the filter curves to shift in step with the shift in resonant frequency caused by temperature, thus ensuring that the normalized difference voltage will be temperature independent. Using the filter circuit for response curve A as an example, it is clear from equation (10) that the center frequency $F_{ch}$ varies with the inverse square root of resistor $r_4$. By replacing resistor $r_4$ with an appropriate negative type thermistor, that is one whose resistance varies inversely with temperature, $F_{ch}$ will vary with the square root of temperature and in step with the resonant frequency shifts caused by temperature. Such a thermistor is best placed within the chamber to provide the most accurate temperature reading. The same type of substitution for $R_4$ in the filter circuit for response curve B will similarly shift $F_{cl}$ in step with the resonant frequency shifts caused by temperature.

The foregoing description is intended to be taken by way of illustration and not of limitation as to the spirit and scope of the invention. While the invention has been described primarily with reference to on-vehicle gasoline vapor sensing, its usefulness is not limited to that particular application.

The embodiments of the invention in which an exclusive property or privilege is claimed are defined as follows:

1. A sensor for detecting concentrations of a gas mixture comprising:
    a chamber bounding the gas mixture, the chamber having a fundamental resonant acoustic frequency varying with the gas concentrations of the mixture therein;
    means for detecting acoustic noise in said chamber and producing therefrom a spectrum signal; and
    means for measuring the fundamental resonant frequency of said chamber from said spectrum signal, said measured fundamental resonant frequency being a measure of the gas concentrations.

2. A sensor for simultaneously detecting concentrations and flow rates of a gas mixture comprising:
    a chamber through which the gas mixture flows, the chamber having an inlet and an outlet and a fundamental resonant acoustic frequency varying with the gas concentrations of the mixture therein;
    means for detecting acoustic noise in said chamber and producing therefrom a spectrum signal;
    means for measuring the fundamental resonant frequency of said chamber from said spectrum signal, said measured fundamental resonant frequency being a measure of the gas concentrations; and
    means for measuring the strength of said spectrum signal, said measured strength being a measure of the gas mixture flow rate corresponding to said gas concentrations.

3. A sensor as claimed in claim 1 or 2 wherein the means for measuring the fundamental resonant frequency comprises:
    first and second frequency filters, each filter having a respective input, output and response curve, each of said response curves having a slope different from the other from a predetermined lowest fundamental resonant frequency to be measured to a predetermined highest fundamental resonant frequency to be measured, both of said filters being commonly coupled to the spectrum signal at their respective inputs; and
    means for measuring a normalized difference between the outputs of the filters, said normalized difference being a measure of the fundamental resonant frequency.

4. A sensor as claimed in claim 3 further comprising:
    means for sensing the temperature of the gas mixture within the chamber; and
    means responsive to said sensed temperature for shifting the response curve of each respective filter to compensate for deviations in the fundamental resonant frequency of the chamber which result from changes in the temperature of the gas mixture within the chamber from a calibration temperature, whereby the measured fundamental resonant frequency is a temperature insensitive measure of the gas concentrations of the mixture.

5. A sensor as claimed in claim 3 wherein the frequency filters are band-pass filters, one of the band-pass filters having a central frequency substantially corresponding to a predetermined lowest fundamental resonant frequency to be measured and the other band-pass filter having a central frequency substantially corresponding to a predetermined highest fundamental resonant frequency to be measured.

6. A sensor as claimed in claim 5 wherein each response curve slope is monotonic from the predetermined lowest fundamental resonant frequency to be measured to the predetermined highest fundamental resonant frequency to be measured.

7. A sensor as claimed in claim 6 wherein the means for measuring the normalized difference comprises:
    means for measuring the difference between the respective outputs of the frequency filters;
    means for measuring the sum of the respective outputs of the frequency filters; and
    means for measuring the ratio of said difference to said sum, said measured ratio being a measure of said normalized difference.

8. A sensor as claimed in claim 3 wherein each response curve slope is monotonic from the predetermined lowest fundamental resonant frequency to be measured to the predetermined highest fundamental resonant frequency to be measured.

9. A sensor as claimed in claim 8 wherein the means for measuring the normalized difference comprises:
    means for measuring the difference between the respective outputs of the frequency filters;
    means for measuring the sum of the respective outputs of the frequency filters; and
    means for measuring the ratio of said difference to said sum, said measured ratio being a measure of said normalized difference.

10. A method for simultaneously detecting concentrations and flow rates of a gas mixture comprising:
    passing the gas mixture through a chamber having an inlet and an outlet and a fundamental resonant acoustic frequency varying with the relative gas concentration of the mixture therein;

detecting acoustic noise in said chamber and producing therefrom a spectrum signal;

measuring the strength of said spectrum signal;

filtering said spectrum signal through a pair of parallel filters to produce a pair of attenuated outputs; and measuring the ratio of the difference between the pair of attenuated outputs to the sum of the pair of attenuated outputs, said measured ratio being a measure of the gas concentrations and said measured strength of the spectrum signal being a measure of the gas mixture flow rate corresponding to said gas concentrations.

* * * * *